US006050951A

United States Patent [19]
Friedman et al.

[11] Patent Number: 6,050,951
[45] Date of Patent: Apr. 18, 2000

[54] NIBP TRIGGER IN RESPONSE TO DETECTED HEART RATE VARIABILITY

[75] Inventors: Bruce Friedman; Lawrence T. Hersh; Richard Medero, all of Tampa, Fla.

[73] Assignee: Critikon Company, L.L.C., Tampa, Fla.

[21] Appl. No.: 08/966,719

[22] Filed: Nov. 10, 1997

[51] Int. Cl.[7] .................................................. A61N 5/00
[52] U.S. Cl. ........................................ 600/485; 128/900
[58] Field of Search ................................. 600/485, 481, 600/487, 488, 493–497; 128/897, 898, 900

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/861 |
| 4,638,810 | 1/1987 | Ramsey, III et al. | 128/681 |
| 4,754,761 | 7/1988 | Ramsey, III et al. | 128/683 |
| 5,052,397 | 10/1991 | Ramsey, III et al. | 128/682 |
| 5,170,795 | 12/1992 | Ramsey, III et al. | 128/682 |
| 5,215,096 | 6/1993 | Zapf et al. | 128/682 |
| 5,285,793 | 2/1994 | Slovut et al. | 600/485 |
| 5,291,400 | 3/1994 | Gilham | 600/509 |
| 5,322,069 | 6/1994 | Gallant et al. | 600/495 |
| 5,518,000 | 5/1996 | Booth et al. | 128/680 |
| 5,533,511 | 7/1996 | Kaspari et al. | 600/485 |
| 5,577,508 | 11/1996 | Medero | 128/681 |
| 5,579,776 | 12/1996 | Medero | 128/680 |
| 5,590,662 | 1/1997 | Hersh et al. | 128/681 |
| 5,606,977 | 3/1997 | Ramsey, III et al. | 128/680 |
| 5,653,241 | 8/1997 | Harada et al. | 600/495 |
| 5,785,659 | 7/1998 | Caro et al. | 600/485 |

OTHER PUBLICATIONS

Akselrod, et al., "Hemodynamic regulation: investigation by spectral analysis," *American Physiological Society*, 1985, pp. 867–875.

Baselli, et al., "Spectral and Cross–Spectral Analysis of Heart Rate and Arterial Blood Pressure Variability Signals," *Computers and Biomedical Research*, vol. 19, 1986, pp. 520–534.

Turjanmaa, et al., "Short–term variability of systolic blood pressure and heart rate in normotensive subjects," *Clinical Physiology*, vol. 10, 1990, pp. 389–401.

*Primary Examiner*—Cary O' Connor
*Assistant Examiner*—Michael Astorino
*Attorney, Agent, or Firm*—Woodcock Washburn Kurtz Mackiewicz & Norris LLP

[57] ABSTRACT

An automated sphygmomanometer which triggers a blood pressure determination upon detection of a significant change in the patient's heart rate variability (HRV). The HRV can be measured directly from the NIBP signal or, when a multiparameter monitor is used, the HRV can be measured from the ECG signal or the NIBP signal. HRV is continuously monitored and the baseline HRV is correlated with baseline blood pressure values. Changes in HRV are displayed continuously on a display so that the clinician can determine whether to initiate an NIBP measurement or, on the other hand, the NIBP measurement can be triggered automatically in response to a change in HRV without any intervention by the clinician. Alternatively, the patient monitor can "learn" the correlation between HRV and blood pressure changes and only alert the clinician when a significant change in HRV has taken place. The technique of the invention allows the clinician to monitor NIBP at less frequent intervals without the concern of missing physiologically significant changes in blood pressure and without the requirement of "check inflates" in a guard mode.

15 Claims, 5 Drawing Sheets

NIBP TRIGGER IN RESPONSE TO DETECTED HEART RATE VARIABILITY

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant signals typically consist of a DC voltage with a small superimposed variational component caused by arterial blood pressure pulsations (referred to herein as "oscillation complexes" or just simply "oscillations"). After suitable filtering to reject the DC component and to provide amplification, peak pulse amplitudes (PPA) above a given base-line are measured and stored. As the decrementing continues, the peak amplitudes will normally increase from a lower level to a relative maximum, and thereafter will decrease. These amplitudes thus form an oscillometric blood pressure envelope for the patient. The lowest cuff pressure at which the oscillations have a maximum value has been found to be representative of the mean arterial pressure ("MAP") of the patient. Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use in an automatic mode, the blood pressure cuff is placed on the patient and the operator sets a time interval, typically from 1 to 90 minutes, at which blood pressure measurements are to be made. The noninvasive blood pressure ("NIBP") monitor automatically starts a blood pressure determination at the end of the set time interval. Typically, the user selects a short interval if the patient is unstable since unstable blood pressure may change to dangerous levels in a short time and selects a longer interval (typically 5-15 minutes) as the patient becomes more stable. The reason a short interval is not used in all cases is that the probability of trauma to the limb from the cuff inflation increases as the determination frequency increases. Similarly, the frequency of blood pressure determinations may be increased as the patient's blood pressure becomes more unstable.

Unfortunately, setting the interval for blood pressure measurement is not an exact science. If it is wrongly assumed that the patient's blood pressure is stable and a long interval is set, critical minutes may pass before dangerous changes in blood pressure are detected. Conversely, if it is wrongly assumed that the patient's blood pressure is volatile, the patient's limb is subjected to many unnecessary cuff inflations and the possible trauma resulting from such cuff inflations. Since a patient's blood pressure can change rapidly, it is desirable to have an early indication that the patient's physiological condition is changing before the blood pressure falls (or rises) to a dangerous level.

One technique for determining when to initiate an oscillometric blood pressure determination based on changes in the patient's physiological condition is described by Ramsey, III et al. in U.S. Pat. No. 5,606,977, also assigned to the present assignee and hereby incorporated by reference in its entirety. In that system, a so-called "guard mode" is used to perform spot-checks of the patient's blood pressure by inflating the patient's cuff only to diastolic pressure and comparing the oscillometric readings at diastolic pressure to those readings obtained for the last full oscillometric measurement. If the readings have changed substantially, a full oscillometric blood pressure determination is immediately conducted; otherwise, the monitor is idle until the next "guard mode" spot check or the next full oscillometric blood pressure measurement at the expiration of the set duration. This approach allows the duration between full oscillometric blood pressure measurements to be lengthened, thereby reducing the discomfort to the patient.

Currently available multi-parameter patient monitors, such as the DINAMAP™ MPS Select Monitor available from Johnson & Johnson Medical, Inc., measure a number of patient parameters besides the patient's blood pressure. For example, the DINAMAP™ MPS Select Monitor also measures a patient's heart rate. In the DINAMAP™ MPS Select Monitor, the patient's heart rate can be derived from the patient's electrocardiogram (ECG), invasive blood pressure (IP) signal, pulse oximetry ($SpO_2$) signal, and noninvasive blood pressure (NIBP) signal. The measured heart rate is then presented on the display, and alarms are sounded if the heart rate is outside of selected upper and lower limits.

Figure 1:
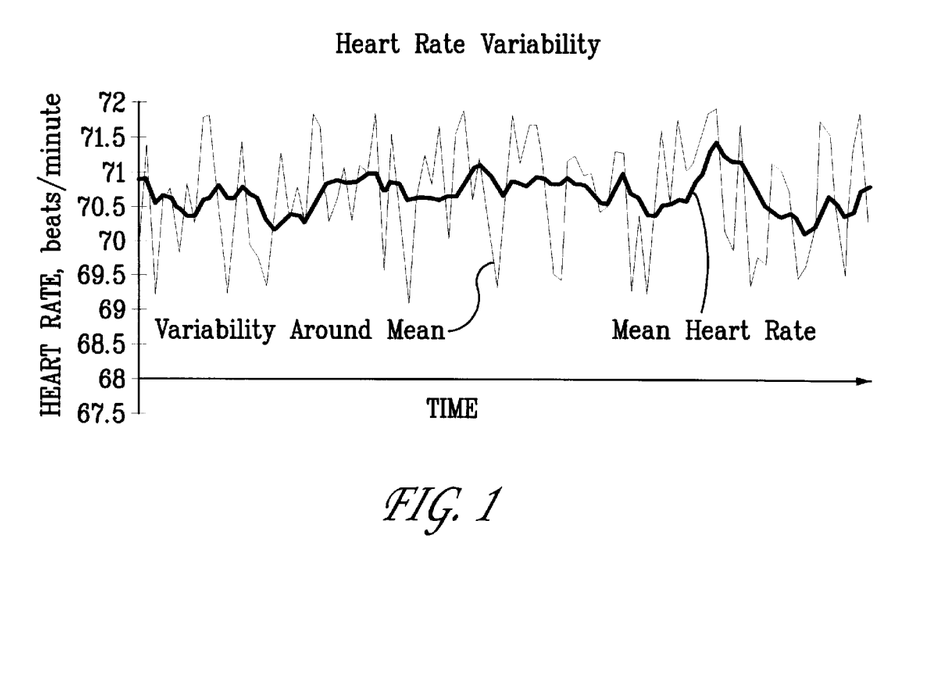
FIG. 1 illustrates heart rate variability in the time domain.
Figure 2:
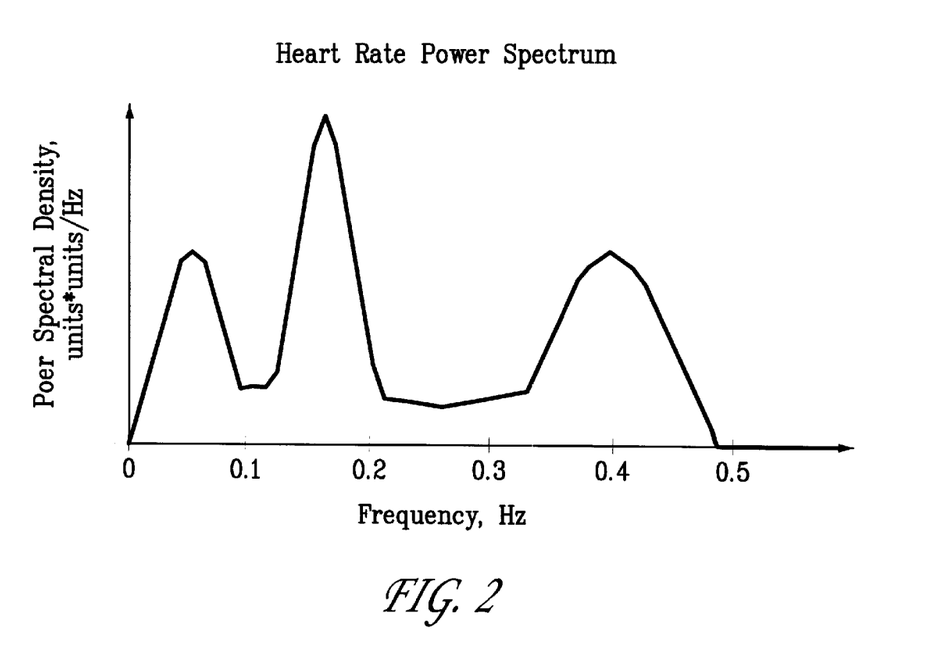
FIG. 2, illustrates heart rate variability in the frequency domain.

Useful physiological information about the patient's condition may be obtained from the heart rate. For example, as shown in FIG. 1, heart rate variability (HRV) is a measure in the change in the R-to-R interval (heart period) from beat to beat. HRV can be measured in the time domain, as in FIG. 1, by taking the standard deviation or calculating the coefficient of variation of the heart rate HR(t), or in the frequency domain, as in FIG. 2, by performing a spectral analysis of HR(t) using an FFT, an autoregressive method, or the like, to determine the power at each frequency to yield the power spectral density (PSD(f)) of the heart rate signal. Assessment of the heart rate and HRV provides information about the functional state of the patient's autonomic nervous system, specifically the balance between sympathetic and parasympathetic innervation. Furthermore, reduced HRV and changed blood pressure variability (BPV) are accepted as risk factors in patients with some cardiovascular diseases, metabolic syndromes or neurologic disorders.

As known by those skilled in the art, the body regulates blood pressure by central and peripheral mechanisms. Central mechanisms include changing the inotropic (contractility) and chronotropic (heart rate) state of the heart. Peripheral mechanisms include changing the compliance and/or resistance of large arteries, small arteries and the microvasculature. These mechanisms are controlled in part by neurologic mechanisms. Significant blood loss during surgery will cause a decrease in blood pressure. The body's afore-mentioned control mechanisms will react to try to compensate for the blood loss to maintain a steady blood pressure. One result of these compensatory mechanisms will be an increase in peripheral resistance. The neural changes required to create this increase in peripheral resistance will result in a change in HRV.

Numerous studies have shown that HRV can be used to assess the risk of sudden cardiac death, to evaluate automatic function in diabetics, and to evaluate the depth of anesthesia. Published studies by Turjanmaa et al. in an article entitled "Short-Term Variability of Systolic Blood Pressure and Heart Rate in Normotensive Subjects," *Clinical Physiology*, Vol. 10, pp. 389–401 (1990), by Baselli et al. in an article entitled "Spectral and Cross-Spectral Analysis of Heart Rate and Arterial Blood Pressure Variability Signals," *Computer and Biomedical Research*, Vol. 19, pp. 520–534 (1986), and by Akselrod et al. in an article entitled "Hemodynamic Regulation: Investigation By Spectral Analysis," *Am. J. Physiol.*, Vol. 249 (Heart Circ. Physiol. 18), pp. H867–H875 (1985), have also shown that changes in HRV are correlated with changes in blood pressure. While Zapf et al. disclose in U.S. Pat. No. 5,215,096 that the time period for measuring for detecting oscillometric complexes at each blood pressure level in the oscillometric method may be varied according to the heart rate of the patient, the present inventors are not aware that detected changes in HRV have been used to predict changes in blood pressure and to trigger a blood pressure determination.

It is, accordingly, a primary object of the present invention to detect changes in the patient's heart rate variability (HRV) to predict changes in blood pressure and to trigger an NIBP blood pressure determination before the patient's blood pressure drops (or rises) to dangerous levels.

It is a further object of the present invention to automatically determine whether the patient's HRV has changed significantly since the last blood pressure determination so that a new blood pressure determination may be instigated immediately upon detection of a significant change in HRV.

It is also an object of the present invention to provide a technique for monitoring the status of the patient's blood pressure between determinations by monitoring the patient's HRV so that a change in the patient's physiological status between blood pressure determinations will not go undetected.

SUMMARY OF THE INVENTION

The above objects have been met in accordance with the present invention by providing an automated sphygmomanometer which triggers a blood pressure determination upon detection of a significant change in the patient's heart rate variability (HRV). The HRV can be measured directly from the NIBP signal or, when a multiparameter monitor is used, the HRV can be measured from the ECG signal or the NIBP signal. In a preferred embodiment, HRV is continuously monitored by monitoring the ECG signal in a multiparameter monitor and correlating the baseline HRV with baseline BP values. Changes in HRV are displayed continuously on a display of the multiparameter monitor so that the clinician can determine whether to initiate an NIBP measurement or, on the other hand, the NIBP measurement can be triggered automatically in response to a change in HRV without any intervention by the clinician. Alternatively, the patient monitor in accordance with the invention could incorporate means for "learning" the correlation between HRV and BP changes and only alerting the clinician when a significant change had taken place.

HRV measurement from the ECG signal is nontraumatic to the patient and does not require the addition of additional sensors to the patient. On the contrary, ECG monitoring is already a standard of care. The system of the invention thus provides the clinician with a means for monitoring rapid changes in a patient's blood pressure or providing an early indicator of blood pressure changes and initiating a blood pressure determination without any of the possible risks or discomforts associated with frequent cuff inflations. Moreover, the technique of the invention allows the clinician to monitor NIBP at less frequent intervals without the concern of missing physiologically significant changes in blood pressure and without the requirement of "check inflates" in a guard mode.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 3–7. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

In U.S. Pat. No. 4,360,029, Ramsey discloses in great detail a system for oscillometric blood pressure monitoring to which the principles of the present invention may be applied with advantage. The disclosure of the commonly assigned Ramsey '029 patent is incorporated by reference herein. The following description of FIG. 3 will act as a brief summary of the operation of that system.

Figure 3:
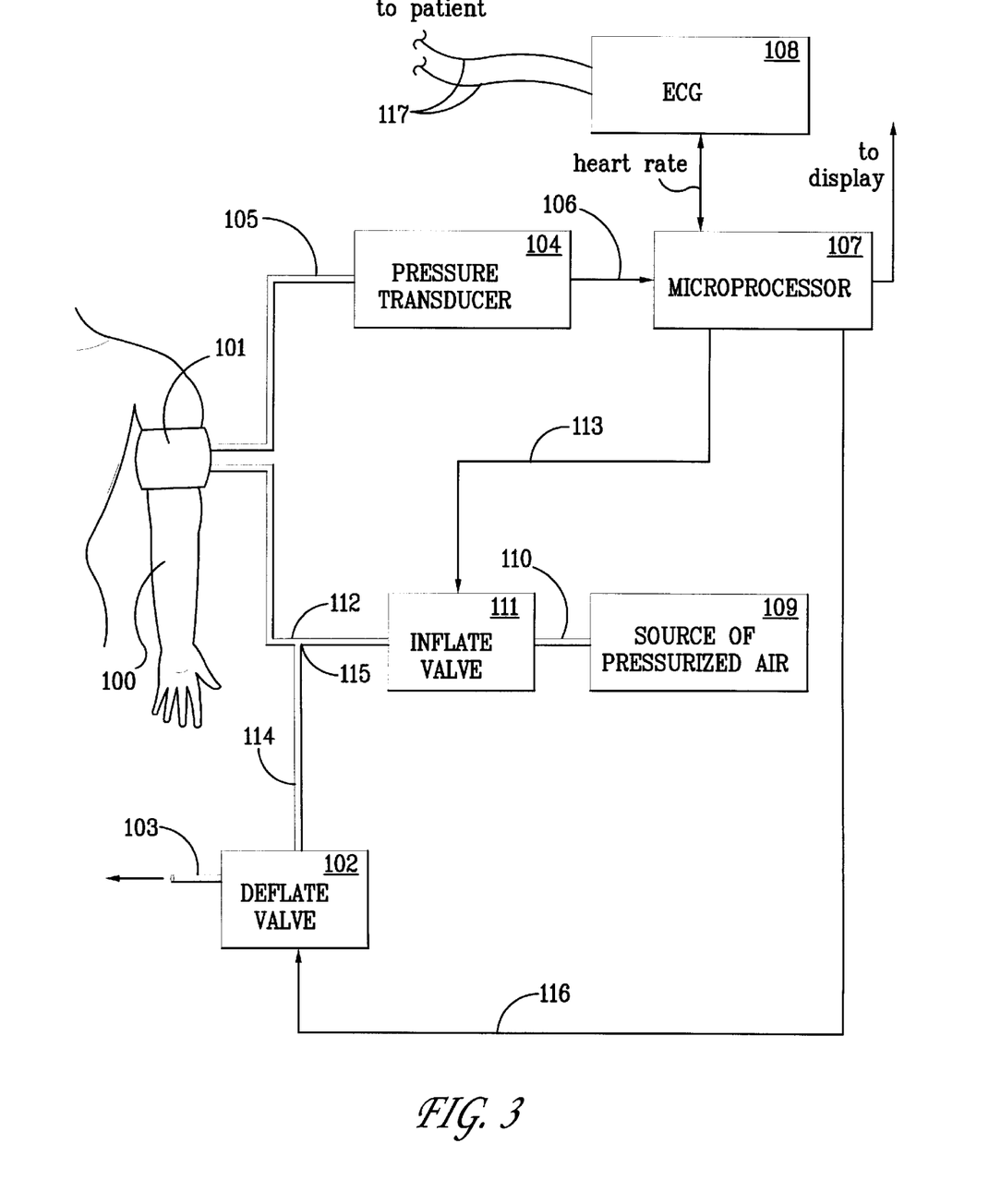
FIG. 3 is a schematic representation of a noninvasive blood pressure ("NIBP") monitor embodying the present invention.

In FIG. 3, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. As will be described more fully below, the deflation of cuff 101 via deflate valve 102 is controlled by microprocessor 107 via control line 116.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101. As will be explained more fully below, an electrocardiogram (ECG) module 108 with leads 117 connected to the patient provides a heart rate signal to the microprocessor 107 for initiating a blood pressure determination when a significant change in heart rate variability (HRV) is detected.

From the standpoint of the principles of the present invention, the processing of the signals from pressure transducer 104 by the microprocessor 107 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al. in U.S. Pat. No. 4,543,962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, of Ramsey, III et al. in U.S. Pat. No. 5,052,397, of Medero in U.S. Pat. No. 5,577,508, and of Hersh et al. in U.S. Pat. No. 5,590,662, all of which are commonly assigned herewith and the disclosures of which are hereby incorporated by reference. In any event, it is desirable to use any of the known techniques to determine the quality of the oscillation complexes received at each level so that the blood pressure determination is made using actual blood pressure data and not artifacts.

The apparatus described above with reference to FIG. 3, except for the programming of the microprocessor 107, can be substantially the same as that disclosed in the Ramsey, III et al. '029 and '034 patents. Thus, during operation of the apparatus illustrated in FIG. 3, it can be assumed that air under pressure to about 8–10 p.s.i. is available in the source of pressurized air 109. When it is desired to initiate a determination of blood pressure, the microprocessor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing the deflate routine.

As noted above, actual measurement of the blood pressure under the control of the microprocessor 107 and the deflate valve 102 as sensed by pressure transducer 104 can be accomplished in any suitable manner such as that disclosed in the aforementioned patents. In addition, the deflation of the cuff 101 can be controlled as described by Booth et al. in U.S. Pat. No. 5,518,000 and by Medero in U.S. Pat. No. 5,579,776, also assigned to the present assignee and the contents of which are hereby incorporated by reference in their entireties. At the completion of each measurement cycle, the deflate valve 102 can be re-opened long enough to relax the cuff pressure substantially completely via exhaust 103. Thereafter, the deflate valve 102 is closed for the start of a new measurement cycle.

By way of a summation, when a blood pressure measurement is desired, the inflate valve 111 is opened while the cuff pressure is supervised by pressure transducer 104 until the cuff pressure reaches the desired level. The inflate valve 111 is then closed. Thereafter, the deflate valve 102 is operated using signal 116 from microprocessor 107 and the blood pressure measurement taken.

Figure 4:
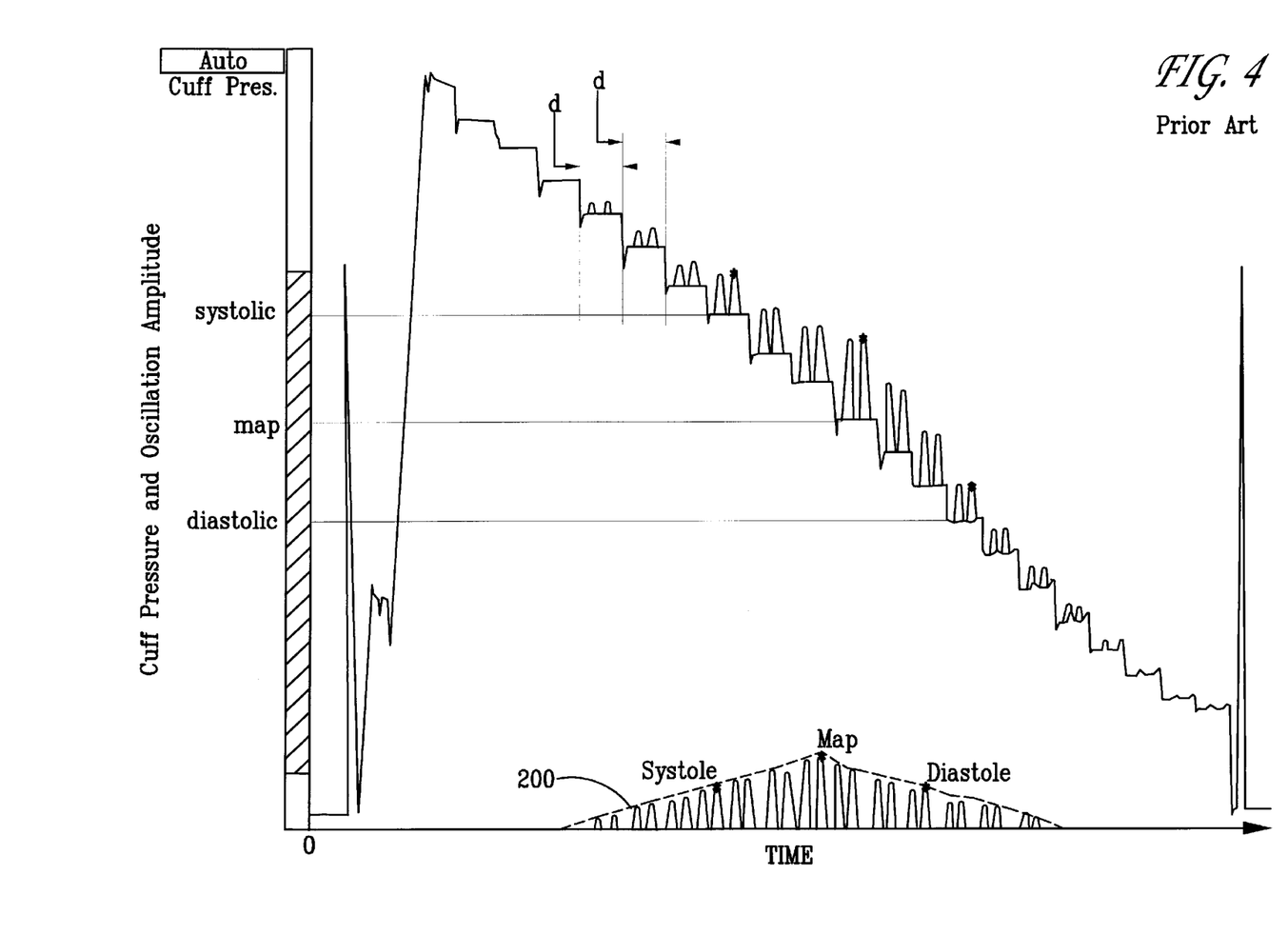
FIG. 4 is a pressure versus time graph illustrating a measuring cycle including step deflation steps and the corresponding oscillation complexes measured using a NIBP monitor in accordance with the invention.

In typical automatic sphygmomanometric devices, the cuff deflation operation is accomplished in equal decrements, usually about 8 mm Hg per step. Prior art FIG. 4 illustrates a pressure versus time graph illustrating a conventional cuff step deflation and measurement cycle for a conventional NIBP monitor. As illustrated, the cuff 101 is inflated to a pressure above the systolic pressure, and the cuff 101 is then deflated in steps of equal duration of about 8 mm Hg per step. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the pressure and searching for oscillation complexes is repeated at least until MAP and/or the oscillometric envelope 200 may be determined. The entire blood pressure determination process is repeated at predetermined set intervals, which are typically set by the user.

To this point, the FIG. 3 monitor operates in a conventional manner. The present invention relates to a technique which monitors the patient's heart rate and instructs the clinician to start, or automatically starts, the above-described oscillometric blood pressure measurement process at times other than the set time intervals when it is determined from the variation in the heart rate (HRV) that the patient's blood pressure has changed or is about to change.

Figure 5:
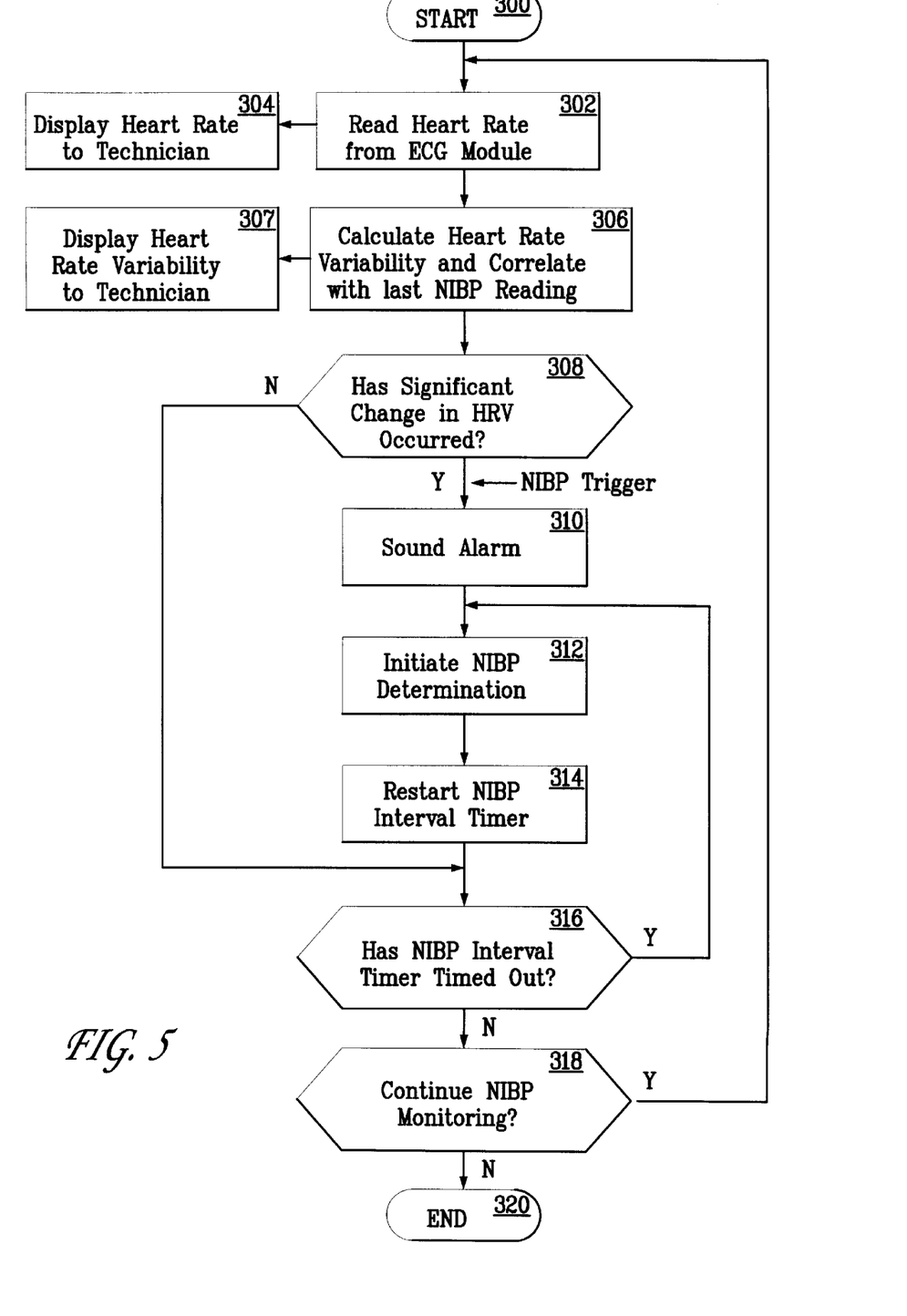
FIG. 5 is a flow chart representing the operation of an NIBP monitor triggered by variations in the patient's heart rate (HRV) in accordance with the invention.

The operation of the HRV NIBP triggering technique in accordance with the invention will now be described with reference to the flow chart of FIG. 5 depicting the NIBP measurement routine in accordance with the invention. Those skilled in the art will appreciate that the flow chart of FIG. 5 is typically implemented in software on microprocessor 107 of FIG. 3 for controlling the triggering of the inflation/deflation and blood pressure measurement cycle.

As noted above, the idea behind triggering a blood pressure determination based on a significant change in heart rate variability is the recognition by the inventors that changes in HRV are correlated with changes in blood pressure and thus can be used to predict changes in blood pressure and, accordingly, to trigger a blood pressure determination at or before the time a significant change in blood pressure occurs. The desired NIBP measurement interval is set prior to entering the NIBP measurement routine of FIG. 5. As noted above, a relatively short NIBP timing interval is set if the patient is unstable, while a progressively longer NIBP timing interval is set as the patient becomes more stable. Then, as illustrated in FIG. 5, the NIBP measurement routine of microprocessor 107 starts at step 300 and reads the most recent heart rate signal provided by ECG module 108 at step 302. Typically, this heart rate is displayed at step 304 to a clinician monitoring the patient.

Next, at step 306, the baseline heart rate variability (HRV) is determined and correlated with the corresponding baseline blood pressure values in a continuous manner. In particular, the HRV is calculated and correlated with the blood pressure values determined at the most recent NIBP measurement stored in system memory. Those skilled in the art will appreciate that HRV may be calculated in one or more of a number of ways, either in the frequency domain or in the time domain.

If sufficient processing power is available, the HRV preferably may be calculated by determining the power spectral density (PSD) of the heart rate signal (HR(t)) using autoregressive techniques, by taking the Fast Fourier Transform (FFT) of HR(t), or using other known techniques for analyzing the frequency content of signals, and then determining the variation in the resulting power spectral density (PSD(f)) using any or all of Equations (1)–(4) below.

Figure 6:
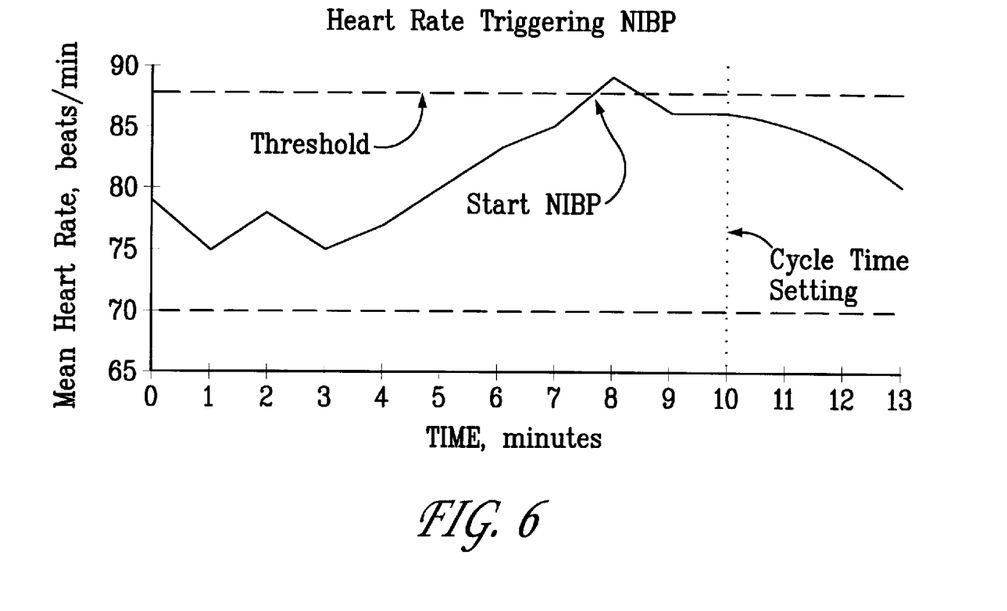
FIG. 6 illustrates a threshold for triggering an NIBP determination based on a change in the patient's heart rate over time.
Figure 7:
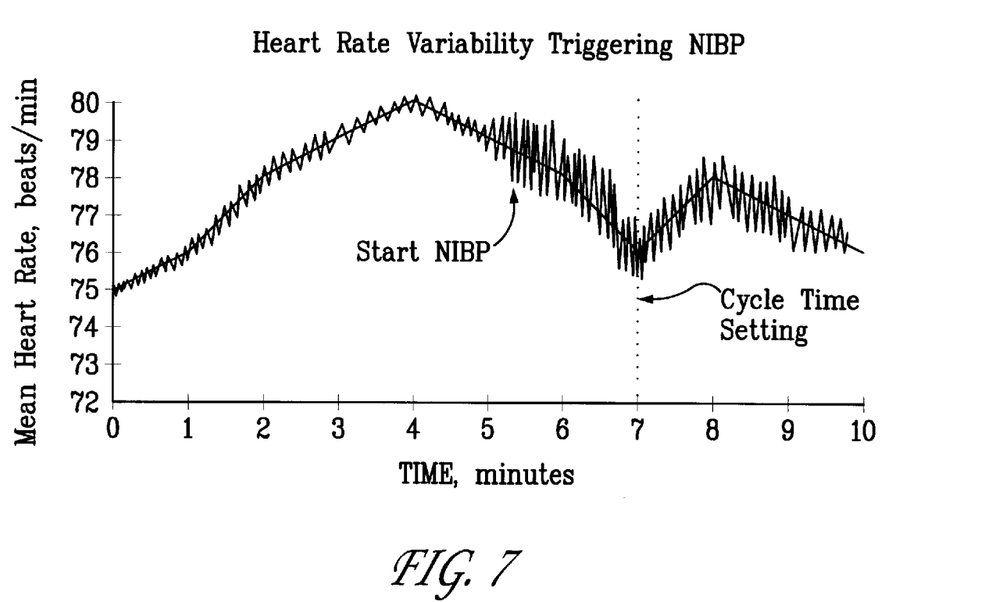
FIG. 7 illustrates a threshold for triggering an NIBP determination based on a change in the patient's heart rate variability over time.

For example, the mean frequency of the PSD(f) of the heart rate may be determined as follows:

$$\bar{f} = \frac{\int_0^\infty f \cdot PSD(f) \cdot df}{\int_0^\infty PSD(f) \cdot df}$$

and an NIBP determination may be initiated if the heart rate exceeds a predetermined heart rate threshold, as illustrated in FIG. 6. Heart rate variability (HRV) then may be calculated by taking the standard deviation of PSD(f) as follows:

$$\delta f^2 = \frac{\int_0^\infty (f - \bar{f})^2 \cdot PSD(f) \cdot df}{\int_0^\infty PSD(f) \cdot df}$$

and initiating an NIBP determination if HRV exceeds a predetermined HRV threshold, as illustrated in FIG. 7. If desired, HRV may be measured in a particular frequency band $f_1$–$f_2$ by first determining the mean frequency in the frequency band $f_1$–$f_2$ as follows:

$$\bar{f}_{12} = \frac{\int_{f_1}^{f_2} f \cdot PSD(f) \cdot df}{\int_{f_1}^{f_2} PSD(f) \cdot df}$$

and then determining the standard deviation of PSD(f) for the frequency band $f_1$–$f_2$ as follows:

$$\delta f_{12}^2 = \frac{\int_{f_1}^{f_2} (f - \bar{f}_{12})^2 \cdot PSD(f) \cdot df}{\int_{f_1}^{f_2} PSD(f) \cdot df}$$

Of course, HRV may be monitored for several frequency bands, depending upon the heart characteristics of the particular patient. Preferably, a frequency band is chosen in which the heart rate variability is most pronounced or best correlated with changes in blood pressure.

On the other hand, if less processing power is available, HRV may be calculated in the time domain by calculating mean heart rate HR as follows:

$$\overline{HR} = \sum_0^N HR_i / N$$

and an NIBP determination may be initiated if the heart rate exceeds a predetermined heart rate threshold, as illustrated in FIG. 6. Then, HRV may be calculated as the standard deviation of the mean heart rate as follows:

$$\partial HR^2 = \sum_0^N (HR_1 - \overline{HR})^2 / (N - 1)$$

and an NIBP determination may be initiated if HRV exceeds a predetermined HRV threshold, as illustrated in FIG. 7.

Any or all of these calculations may be made to determine if any of the calculations results in a significant change in heart rate or HRV. Ideally, changes in the heart rate and HRV as so determined are displayed continuously to the clinician at 307 so that the clinician can empirically determine whether to initiate an NIBP measurement.

Other known methods of evaluating changes in the frequency content of the heart rate or HRV signals can be used to determine the threshold for initiating an NIBP measurement. One example is to compare the changes in the power content of the heart rate or HRV signals within certain frequency bands representing known physiological mechanisms.

Preferably, at step 306, the heart rate variability values so determined are correlated with the stored blood pressure values using known techniques so that corresponding changes in blood pressure may be predicted for measured changes in HRV.

Next, at step 308, it is determined whether the HRV has a value above the determined threshold and is thus sufficient to trigger an NIBP determination, as exhibited by way of example in FIG. 7. For example, it is determined whether HRV exhibits a predetermined percentage change (e.g., 20%) from the mean heart rate sufficient to warrant initiation of an immediate NIBP determination. If a significant change in heart rate (HRV) is detected (i.e., the change is above the predetermined threshold), then an NIBP trigger signal is generated and an alarm may be optionally sounded at step 310 to alert the clinician that an NIBP measurement should be initiated at step 312. An NIBP determination then may be automatically initiated at step 312 if it is determined that a significant change in HRV has occurred that correlates with a change in blood pressure. On the other hand, the clinician can initiate the NIBP determination at step 312 upon viewing a significant change in HRV on the display monitor. In either case, an NIBP determination as described above with respect to FIGS. 3 and 4 is performed at step 312. At the conclusion of an NIBP determination at step 312, the NIBP interval timer is restarted at step 314 to reflect that an NIBP determination just occurred and that the next scheduled NIBP determination is not to occur until the expiration of the NIBP timing interval set by the clinician. Alternatively, the NIBP timing interval could continue to count so that the NIBP determination triggered by the change in HRV would be in addition to the normally scheduled NIBP determination.

If it is determined at step 308 that no significant change in HRV has occurred, or if an NIBP determination has just been initiated at step 312, then microprocessor 107 checks at step 316 to determine if it is time to initiate another NIBP determination. If so, an NIBP determination is initiated at step 312; otherwise, microprocessor 107 checks at step 318 to determine if the NIBP monitoring is to continue (i.e., no power off signal has been received and the cuff 101 has not been disconnected). If NIBP monitoring is to continue, the heart rate is again determined at step 302 and the process repeats. Otherwise, the NIBP monitoring routine is exited at step 320.

In a presently preferred embodiment of the invention, a blood pressure determination is automatically triggered at step 312 if the change in HRV correlates to a change in blood pressure of greater than 20 mm Hg, and the predetermined threshold is set accordingly. Of course, other thresholds may be set as desired to minimize the number of false positives and the number of false negatives.

It will be appreciated by those skilled in the art that by triggering NIBP determinations based on changes in HRV in accordance with the invention, the set time for the conventional NIBP determinations may be extended, thereby minimizing the trauma to the patient's limb and reducing the risk and discomfort to the patient.

It also will be appreciated by those skilled in the art that the foregoing has set forth an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic pressure as described, for example, in U.S. Pat. No. 4,461,266 to Hood et al. Also, those skilled in the art will appreciate that the techniques of the invention may be used for blood pressure monitors which do not use the amplitude matching techniques described by Ramsey et al. to determine whether oscillation complexes of sufficient quality have been received. The method of the invention can also be applied to blood pressure monitors using other techniques for measuring blood pressure besides the oscillometric method, such as the pulse wave velocity technique and the like. In addition, while the heart rate is preferably detected from the QRS complexes detected by an ECG monitor of a multiparameter patient monitor, the heart rate may also be detected using a plethysmograph, an oxygen saturation transducer, or any other suitable device which can measure variations in the heart rate. Accordingly, all such modifications are intended to be included within the scope of the appended claims.

We claim:

1. An automated sphygmomanometer apparatus, comprising:

a blood pressure measurement apparatus which measures a patient's blood pressure using a noninvasive blood pressure cuff;

a heart rate variability monitor which monitors variations in the patient's heart rate without inflating said blood pressure cuff; and control means for initiating a blood pressure measurement by said blood pressure measurement apparatus when said heart rate variability monitor indicates that the patient's heart rate has varied a predetermined amount over a predetermined period of time, said predetermined amount of heart rate variability correlating to a predetermined percentage chance in the patient's blood pressure.

2. An apparatus as in claim 1, wherein said blood pressure measurement apparatus in an oscillometric blood pressure monitor comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any blood pressure oscillations therein; and deflating means operatively coupled to said cuff for selectively relieving pressure from said cuff.

3. An apparatus as in claim 1, wherein said heart rate variability monitor comprises an electrocardiograph and a display which displays the patient's heart rate.

4. An apparatus as in claim 1, wherein said control means automatically initiates said blood pressure measurement by issuing a trigger signal to said blood pressure measurement apparatus upon detection of said predetermined amount of variation in the patient's heart rate over said predetermined period of time.

5. An apparatus as in claim 4, wherein said control means calculates a mean heart rate over said predetermined period of time and calculates said variability of said heart rate as a standard deviation of said mean heart rate over said predetermined period of time.

6. An apparatus as in claim 4, wherein said control means calculates a power spectral density of said heart rate over a predetermined frequency range, calculates a mean frequency over said predetermined frequency range, and calculates said variability of said heart rate as a standard deviation of said mean frequency over said predetermined frequency range.

7. An apparatus as in claim 4, wherein said control means correlates said heart rate variation with measured blood pressure values and issues said trigger signal if said heart rate variation correlates with a predetermined percentage change in blood pressure.

8. An automatic oscillometric blood pressure monitor comprising:

a pressurized cuff;

means for inflating and deflating said cuff;

means for measuring arterial pressure oscillation complexes through measurement of time varying pressures within said cuff;

means for determining the patient's blood pressure at predetermined intervals by instructing said inflating and deflating means to inflate said cuff about an artery of a patient until said cuff is at a pressure level above the patient's estimated systolic pressure and to deflate said cuff by predetermined pressure decrements, by searching for arterial pressure oscillation complexes at each pressure level, and by determining, from said arterial pressure oscillation complexes, parameters representative of at least a portion of an oscillometric envelope of the patient;

means for detecting variations in the patient's heart rate without inflating said cuff; and means responsive to said heart rate variations detecting means for immediately initiating a blood pressure determination by said blood pressure determining means prior to the expiration of any of said predetermined intervals if said detecting means detects variations in the patient's heart rate which correlate to a predetermined percentage change in the patient's blood pressure.

9. A monitor as in claim 8, wherein said predetermined percentage change in the patient's blood pressure is 20%.

10. A monitor as in claim 8, wherein said heart rate variations detecting means comprises an electrocardiograph and a display which displays the patient's heart rate.

11. A monitor as in claim 8, wherein said blood pressure determination initiating means automatically initiates a blood pressure determination by issuing a trigger signal to said inflating and deflating means upon detection of a heart rate variation which correlates to said predetermined percentage change in the patient's blood pressure.

12. A monitor as in claim 8, wherein said blood pressure determination initiating means calculates a mean heart rate over a predetermined period of time and calculates variations of said heart rate as a standard deviation of said mean heart rate over said predetermined period of time.

13. A monitor as in claim 8, wherein said blood pressure determination initiating means calculates a power spectral density of said heart rate over a predetermined frequency range, calculates a mean frequency over said predetermined frequency range, and calculates said variations of said heart rate as a standard deviation of said mean frequency over said predetermined frequency range.

14. A method of monitoring a patient's blood pressure, comprising the steps of:

determining, at predetermined intervals, the patient's blood pressure using a noninvasive blood pressure cuff;

continuously determining the patient's heart rate and continuously monitoring variations in said heart rate without inflating said cuff;

correlating variations in the patient's heart rate with changes in the patient's blood pressure; and initiating a blood pressure determination prior to the expiration of any of said predetermined intervals if variations in the patient's heart rate are determined in said correlating step to correlate to a predetermined percentage change in the patient's blood pressure.

15. In an automatic oscillometric blood pressure monitor comprising a pressurized cuff, means for inflating and deflating said cuff, means for measuring arterial pressure oscillation complexes through measurement of time varying pressures within said cuff, and means for determining a patient's blood pressure at predetermined intervals by instructing said inflating and deflating means to inflate said cuff about an artery of the patient until said cuff is at a pressure level above the patient's estimated systolic pressure and to deflate said cuff by predetermined pressure decrements, by searching for arterial pressure oscillation complexes at each pressure level, and by determining, from said arterial pressure oscillation complexes an oscillometric envelope of the patient, a method of monitoring a patient's blood pressure comprising the steps of:

determining the patient's heart rate without inflating said cuff;

monitoring variations in said heart rate;

correlating variations in said heart rate with variations in the patient's blood pressure; and initiating a blood pressure determination by said oscillometric blood pressure monitor prior to the expiration of any of said predetermined intervals if variations in the patient's heart rate correlate to a predetermined percentage change in the patient's blood pressure.

* * * * *